United States Patent
De Santi Ungarato et al.

(10) Patent No.: US 12,415,147 B2
(45) Date of Patent: Sep. 16, 2025

(54) FOAM CONTROL AGENT

(71) Applicant: Dow Global Technologies LLC, Midland, MI (US)

(72) Inventors: Rafael F. De Santi Ungarato, Jundiaí (BR); Xue Chen, Manvel, TX (US); Ellen D. Costa, Jundiaí (BR)

(73) Assignee: Dow Global Technologies LLC, Midland, MI (US)

(*) Notice: Subject to any disclaimer, the term of this patent is extended or adjusted under 35 U.S.C. 154(b) by 388 days.

(21) Appl. No.: 17/995,460

(22) PCT Filed: Apr. 13, 2021

(86) PCT No.: PCT/US2021/026943
§ 371 (c)(1),
(2) Date: Oct. 4, 2022

(87) PCT Pub. No.: WO2021/211482
PCT Pub. Date: Oct. 21, 2021

(65) Prior Publication Data
US 2023/0415074 A1    Dec. 28, 2023

Related U.S. Application Data

(60) Provisional application No. 63/009,630, filed on Apr. 14, 2020.

(51) Int. Cl.
*B01D 19/04* (2006.01)
*C07C 43/11* (2006.01)
*C12P 7/06* (2006.01)

(52) U.S. Cl.
CPC ..... *B01D 19/0404* (2013.01); *B01D 19/0409* (2013.01); *C07C 43/11* (2013.01); *C12P 7/06* (2013.01)

(58) Field of Classification Search
CPC . B01D 19/0404; B01D 19/0409; C07C 43/11; C12P 7/06
See application file for complete search history.

(56) References Cited

U.S. PATENT DOCUMENTS

| | | | |
|---|---|---|---|
| 9,018,266 B2 | 4/2015 | Matani et al. | |
| 9,150,886 B2* | 10/2015 | Oliveira | C12P 7/06 |
| 2007/0238905 A1* | 10/2007 | Arredondo | C07C 41/09 |
| | | | 568/672 |
| 2010/0075389 A1 | 3/2010 | Wurm et al. | |

(Continued)

FOREIGN PATENT DOCUMENTS

| CN | 101376089 B | 9/2010 |
|---|---|---|
| GB | 1539625 A | 1/1979 |

(Continued)

OTHER PUBLICATIONS

PubChem. "SID 128684577". https://pubchem.ncbi.nlm.nih.gov/substance/128684577. (Year: 2011).*

(Continued)

*Primary Examiner* — Angela C Brown-Pettigrew
*Assistant Examiner* — Brittany Sharon Harris

(57) ABSTRACT

A foam control agent and method of controlling foam for bioethanol processing by use of a foam control agent, wherein the agent comprises at least a (poly)glycerol ether.

7 Claims, 1 Drawing Sheet

(56) References Cited

U.S. PATENT DOCUMENTS

2016/0145647 A1* 5/2016 de Oliveira Lino ..... C12N 1/34
435/161
2017/0349916 A1* 12/2017 Nagamatsu ............... C12P 7/10

FOREIGN PATENT DOCUMENTS

| JP | 2017506154 A | * | 3/2017 | ............ | C11D 3/162 |
| KR | 101769847 B1 | * | 8/2017 | ............ | C07C 29/78 |

OTHER PUBLICATIONS

Junker, "Review: Foam and Its Mitigation in Fermentation Systems"; Biotechno. Prog., 2007, vol. 23, pp. 767-784.
PCT/US2021/026943, International Search Report and Written Opinion with a mailing date of Jul. 27, 2021.

* cited by examiner

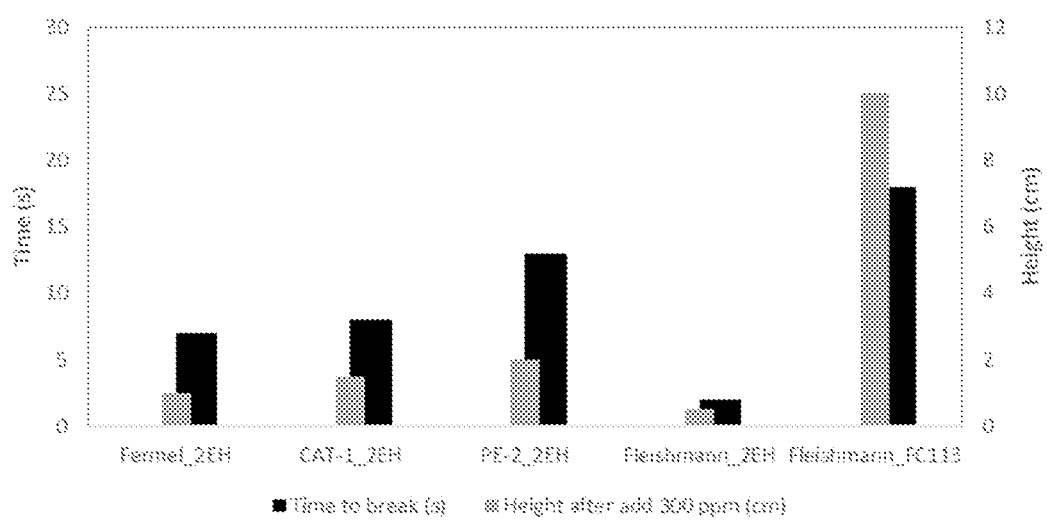

FOAM CONTROL AGENT

Embodiments relate to a foam control agent and method of controlling foam for bioethanol processing, wherein the agent comprises at least a (poly)glycerol ether.

INTRODUCTION

Ethanol may be produced through a biological fermentation process from sugarcane feedstocks. Such ethanol is termed bioethanol (sometimes noted as bio-ethanol) and the process to produce this ethanol is frequently bogged down by the presence of foam created by yeasts in the production media. The yeasts are added to a fermentation tank with a continuous supply of the sugarcane feedstocks to produce bioethanol. Uncontrolled foaming in these tanks can result in a significant loss in production capacity. The foaming can cause inefficient mixing or pumping, clogged process lines, and/or overflows which result in spills and product waste. Foaming during ethanol production is a major challenge and thus mechanical methods of foam management have been devised with limited effectiveness.

Foam control agents (FCA) are widely considered more practical than the mechanical methods and are currently more commonly employed across the industry to minimize production losses due to foaming. These foam control agents can include both defoaming and anti-foaming chemicals. Antifoamers (a term of art) are designed to prevent foam, whereas defoamers (another term of art) eliminate existing foam.

For fermentation applications, foam control agents typically include block copolymers composed of ethylene oxide, propylene oxide, polypropylene glycol, and/or butylene oxide. These types of products are effective since, it is believed that at increased temperatures, they are insoluble in solution, thereby causing an increase in the surface tension of the system, which results in foam collapse. Generally, these materials are combined with other hydrophobic materials to improve the foam control properties. The use of these foam control agents is critical to the industry and thus any novel or improved foam control agent is highly useful.

For all these reasons and more, there is a need for a foam control agent and method of controlling foam for bioethanol processing.

SUMMARY

Embodiments relate to a foam control agent and method of controlling foam for bioethanol processing, wherein the agent comprises at least a (poly)glycerol ether.

BRIEF DESCRIPTION OF THE DRAWING

FIG. 1 is a bar graph showing the results of times to break the foam (defoaming effect) after the presently disclosed agent's application to four different yeast strains.

DETAILED DESCRIPTION

The present disclosure relates to a foam control agent for bioethanol production. As previously discussed, ethylene oxide, propylene oxide, and/or butylene oxide are commonly used foam control agents. The present disclosure details how glycerin ethers or (poly)glycerol ether (e.g., 2-EH glycerol or 2-Ethylhexyl glycerol ether or 3-(2-ethylhexyloxy)-1,2-propanediol) have been discovered to have a superior foam control performance as both a defoaming agent and antifoaming agent. In one embodiment, these chemicals may be obtained by reductive etherification between glycerin and fatty alcohol. Other methods of production may also be utilized and the reductive etherification method above is a non-limiting example.

The use of glycerin ethers as foam control agents may also be utilized in conjunction with copolymers composed of ethylene oxide, propylene oxide, and/or butylene oxide, or other hydrophobic materials such as waxes or silicas. The use of glycerin ethers as foam control agents may also be utilized in conjunction with silicone foam control agents. These additional chemicals present in a foam control agent may also be added with branched alcohols and/or surfactants (especially alkoxylates of the alcohols). The use of glycerin ethers as foam control agents can be water based or oil based.

The concentration of glycerin ethers in the formulated foam control agent may range from 0.1% to 100% by weight, with preferred embodiments for antifoaming use ranging from 1% to 100% by weight. When used as a defoaming foam control agent, a preferred embodiment may feature a concentration of glycerin ethers that ranges from 1% to 100%. Put another way, the usage dosage of the novel foam control agent ranges from 5 to 10000 ppm in relation to the total amount of materials present in a given fermentation tank. When the agent is used for its antifoaming properties, one preferred embodiment has a dosage range from 5 to 100000 ppm. When used as defoaming agent, an embodiment utilizes a dosage range from 10 to 500000 ppm, more preferably from 50 to 10000 ppm. It should be noted that the preferred ranges discussed above are not limiting and the use of the glycerin ether containing foam control agent may be useful at even 1 ppm or less depending on how the novel agent is utilized in the presence of other foam control agents, etc. Some common ranges for antifoam usage of the present agent are 200-500 ppm and 400-1000 ppm for defoaming use (twice the antifoam concentration).

The new foam control agent presently disclosed may be in the form of a solid or liquid. If it is a solid, the material may be dissolved or dispersed in a solvent before use as a foam control agent. The presently disclosed agents are believed to work in the presence of all commonly used bioethanol fermentation yeasts that can generate foam including, but not limited to, different strains of: Saccharomyces Cerevisiae, Candida Albicans, Schizosaccharomyces, Brettanomyces and others.

A generalized, generic structure of the presently disclosed (poly)glycerol ether foam control agent is as follows:

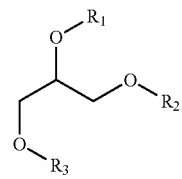

Where R1, R2 and R3 can independently be an alkyl group. R1, R2 or R3 may also be a hydrogen atom, however, in this embodiment they should not all be a hydrogen atom. In one preferred embodiment, R1 may be an alkyl group or aryl alkyl group with the number of carbon atoms ranging from C8-C32 (linear or branched) and R2 and R3 are independently hydrogen or a polyether group.

The structure above may be further modified and/or expanded as follows:

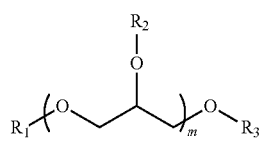

In this embodiment, m may be an integer from 1 to 10. R1, R2, and R3 may each independently have a number of carbon atoms from 0 to 30. R1, R2, and R3 may also independently be comprised of an alkyl group or an aryl alkyl group. The alkyl group(s) may be linear, branched, or cyclic. R1, R2, and R3 may also be a hydrogen atom, however, in this embodiment they should not all be a hydrogen atom.

The chemical agent can be used both in antifoamer or defoamer formulations. Antifoamer formulations are obtained by the mixture of polyglycols, esters, silicones, solvents, water and other chemicals that in the gas-liquid interface of the bubble avoiding the foam formation. Other amphiphilic chemicals based on block copolymer can be used as well. In defoaming formulations, in addition to the products mentioned above, it can be used vegetal oils, mineral oils, waxes and other oily agents.

The currently disclosed chemical can be used as a booster or the main component of such formulations and it can be used to prevent or breakdown the foam. In sugarcane mills this means that the product can be used in yeast treatment tanks or in fermentation tank themselves. It can be used continuously or batched, being highly suitable for any type of mill operation.

This chemical can be added in the tank, where the yeast is treated with acid and other chemicals; or be added in the fermentation tank before, during, or after the addition of the sugar solution. Fermentation is usually conducted at temperatures lower than 34° C. This temperature is obtained by the use of heat exchangers. After the dispersion of yeast has been transferred to the fermentation tank, the feed of the sugar solution can take a good deal of time (up to 6 or 8 hours) and during this time period is where the greatest foaming occurs. After the sugar solution feeding, some additional time can be required to ensure an effective conversion of sugar in ethanol. This additional period can vary from 1-4 hours for to a total time of 12 hours from the beginning of the feeding of the sugar solution. The current product is indicated to be used during the entire duration of the fermentation process.

EXAMPLES

An experiment to test the efficacy of the presently disclosed foam control agent and others may be conducted using Fermentest equipment as follows. The chemicals used as foam control agents are commercially available from The Dow chemical Company under the trademarks of FLUENT-CANE™ and POWERCANE™. The 2-EH glycerol ether was synthesized following the below procedure. 2-Ethylhexanal (128.2 g, 1 mol), glycerol (920.9 g, 10 mol), and 5% Pd/C catalyst (5 wt % relative to the aldehyde, 6.41 g) (each of which were purchased from Sigma-Aldrich) were loaded under nitrogen into a 2 L Parr reactor. The reactor was sealed and purged with hydrogen three times at about 100 psi with stirring. Then hydrogen (100 psi) was charged, the reactor was quickly heated to 200° C. with stirring, and hydrogen pressure was set at 500 psi. The reaction was carried out for 14 hours at 200° C. and 500 psi of hydrogen.

The catalyst was filtered off and washed with methanol, the solvent was evaporated in vacuum. The upper (product) phase was separated and the lower (glycerol) phase was extracted with toluene (300 mL×6). Toluene was evaporated and the residue was combined with the product phase to give the crude product (178.4 g), a part of which (128.4 g) was fractionally distilled in vacuum to give 103.7 g (71%) of 3-(2-ethylhexyloxy)-1,2-propanediol (major) and 2-(2-ethylhexyloxy)-1,3-propanediol (minor, 2-EH glycerol ether), b.p. 82-84° C./0.06 mm Hg.

The different strain yeasts used were obtained from LNF, a local company in Brazil. For all experiments, a 20 wt % sugar solution is created with tap water, in order to obtain 20 Degrees Brix (° Bx) along with 10 wt % yeast (a strain of Saccharomyces Cerevisiae, also diluted in tap water). A certain amount (e.g., 0.135 g) of the glycol (or another foam control agent) is then added into the mixture of 300 g of the yeast preparation and 600 g of the sugar solution. In this example, the addition of 0.135 g of foam control agent amounts to around 150 ppm foam control agent in relation to total weight of 900 g of the solutions added into Fermentest equipment. The total mass was then transferred to a cylindrical vessel, in which air was injected via a porous plate.

After this, a 7.0 L/min airflow rate was passed through the porous plate (16-40 μm pore size) and the time required for the foam to reach 25 cm height was measured. This demonstrated the differences in foam behavior and in the ability of each tested agent to retain the foam height in comparison with each yeast strain. The longer the time to reach the foam height, the better the product performance. This parameter is represented as Time to 25 cm (T25) in Table 1. A blank, without the addition of any foam control chemicals, was also run as a control in order to have a better comparison for analysis of the results which were obtained in triplicates and are shown below.

TABLE 1

| Experiments | Products | Concentration (ppm) | Time to height of 15 cm (s) | Time to height of 20 cm (s) | Time to height of 25 cm (s) |
|---|---|---|---|---|---|
| Comparative example 1 | Blank | 0 | 17 | 24 | 30 |
| Comparative example 2 | FLUENT-CANE ™ 178 | 150 | 63.0 | 81.8 | 102.1 |
| Comparative example 3 | POWERCANE ™ 278 | 150 | 103.9 | >300 | >300 |
| Comparative example 4 | POWERCANE ™ 278 | 100 | 105.4 | 176.4 | >300 |
| Example 1 | 2-EH glycerol ether | 100 | 45.1 | 96.6 | >300 |

In Table 1, the higher the values of time, the better the product performance, therefore: 2-EH glycerol ether, POWERCANE™ 278 (PC 278) was the chemicals able to avoid foam formation (antifoaming effect) at the concentration of 100 ppm until 300 seconds of experiment. It is also possible to see from these results that even in a higher concentration FLUENT-CANE™ 178 was not able to completely avoid foam formation.

In order to further evaluate the performance of these foam control agents, another set of experiments was performed, similar to the ones discussed above, but altered by first adding 150 ppm (0.135 g) of FLUENT-CANE™ 178 as an antifoaming agent and then, when the foams reached the height of 20 cm in the cylindrical vessel, 300 ppm (0.27 g) of the various test agents were added to break the foam. The minimum height after the addition of each product and the necessary time to break the foam at the minimum height, were recorded in the tables and charts below.

TABLE 2

| Experiment | Yeast | Antifoamer | Concentration Antifoamer (ppm) | Defoamer | Concentration (ppm) | Time to break (s) | Height after add 300 ppm (cm) |
|---|---|---|---|---|---|---|---|
| Example 2 | Fermel | FLUENT-CANE™ 178 | 150 | 2-EH glycerol ether | 300 ppm | 7 | 1 |
| Example 3 | CAT-1 | FLUENT-CANE™ 178 | 150 | 2-EH glycerol ether | 300 ppm | 8 | 1.5 |
| Example 4 | PE-2 | FLUENT-CANE™ 178 | 150 | 2-EH glycerol ether | 300 ppm | 13 | 2 |
| Example 5 | Fleishmann | FLUENT-CANE™ 178 | 150 | 2-EH glycerol ether | 300 ppm | 2 | 0.5 |
| Comparative example 5 | Fleishmann | FLUENT-CANE™ 178 | 150 | FLUENT-CANE™ 113 | 300 ppm | 18 | 10 |

FIG. 1 shows the results of times to break the foam (defoaming effect) after the presently disclosed agent's application to four different yeast strains (Fermel, CAT-1, PE-2 and Fleishmann) 2EH is short-hand for 2-EH glycerol ether. Also shown in FIG. 1 are the results of height obtained after the 2-EH glycerol ether was added and broke the foam formation.

Table 2 lists the results of times to break a formed foam and the results of the height obtained after the addition of 2-EH glycerol ether in comparison to FLUENT-CANE™ 113. The novel agent was able to knock down the foam almost immediately (within 2 seconds) after its addition to all four of the yeast strains evaluated. This performance was not observed in any other case. In contrast, when FLUENT-CANE™ 113 was used for knocking down the foam in the presence of Fleishmann yeast, the final height obtained was 10 cm and it took almost 25 seconds to happen.

As seen in this example, a foam control agent for bio-ethanol processing which contains a (poly)glycerol ether (e.g., 2-EH glycerol ether) provides dramatically improved foam control over the existing foam control agents.

The invention claimed is:

1. A method of controlling foam for bioethanol processing comprising the step of adding a foam control agent to a fermentation process for manufacturing bioethanol, wherein the foam control agent comprises 2-ethylhexyl glycerol ether.

2. The method of claim 1, wherein at least one other foam control agent or hydrophobic material is added to the fermentation process.

3. The method of claim 1, wherein a silicon defoamer or surfactant is also added to the fermentation process.

4. The method of claim 1, where the foam control agent is added to a tank where yeast is treated with acid.

5. The method of claim 1, where the foam control agent is added to a fermentation tank.

6. The method of claim 1 where the 2-ethylhexyl glycerol ether concentration ranges from 0.1 to 100 wt % of the foam control agent by weight.

7. The method of claim 5 where the 2-ethylhexyl glycerol ether concentration is 1 to 500000 ppm in the fermentation tank.

* * * * *